US00PP09409P

United States Patent [19]

Rother

[11] Patent Number: Plant 9,409

[45] Date of Patent: Dec. 26, 1995

[54] PETUNIA PLANT NAMED 'SWEET VICTORY'

[76] Inventor: Reinhard W. Rother, 56 Monhulk Emerald Road, Emerald, Victoria 3782, Australia

[21] Appl. No.: 193,437

[22] Filed: Feb. 8, 1994

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,722 | 4/1989 | De Jong | Plt./68.1 |
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 7,150 | 2/1990 | Vletter | Plt./68.1 |
| P.P. 7,224 | 5/1990 | Rosendal | Plt./68.1 |
| P.P. 7,270 | 7/1990 | Schwyn | Plt./68.1 |
| P.P. 7,344 | 10/1990 | Bloom et al. | Plt./68.1 |
| P.P. 7,400 | 12/1990 | Tvrtkovic-Sahin et al. | Plt./68.1 |
| P.P. 7,544 | 6/1991 | Lamont | Plt./68.1 |
| P.P. 8,015 | 10/1992 | Falstad, III | Plt./68.1 |
| P.P. 8,158 | 2/1993 | Dehan | Plt./68.1 |
| P.P. 8,352 | 8/1993 | Zemach | Plt./68.1 |
| P.P. 8,388 | 9/1993 | Akerboom | Plt./68.1 |

OTHER PUBLICATIONS

Heiser et al., Nightshades The Paradoxical Plants, W. H. Freeman and Co. Publisher (1969).

Milne, Lorus and Margery, Living Plants of the World, Random House, N.Y. Publisher (1975).

Simpson and Conner–Ogorzaly, Economic Botany—Plants in Our World, McGraw–Hill Book Co. Publisher (1986).

*Primary Examiner*—James R. Feyrer

*Attorney, Agent, or Firm*—Brown, Martin, Haller & McClain

[57] ABSTRACT

A new and distinct variety of *Petunia axillaris* plant called "Sweet Victory" is described. The variety is a prostrate, diffuse spreading, viscid glandular pubescent perennial with spreading or handing leaves reaching a length of 1 meter or more. The leaves are ovate and approximately 2–6 cm long×1–2 cm wide; early leaves are commonly larger than later leaves and some early leaves are exceptionally large. The salverform, pendulous flowers have a red purple corolla, purple violet backs of the petals and tube, and blue veins of petals and tube. The variety is tolerant of a wide range of temperatures, especially higher temperatures, has a high growth rate and is ever blooming with a high concentration of blooms.

1 Drawing Sheet

BACKGROUND OF THE VARIETY

The present invention relates to a new and distinct variety of petunia plant which is obtained by clonal selection from a number of seedlings originally obtained by open pollination of parent clones.

Petunias are popular plants widely used as ornamentals for bedding and potting during the summer growth season. There are numerous varieties which exhibit a wide range of properties. However, petunias normally have moderate growth rates, are annuals, grown from seed, have only moderate bloom concentration per plant, and are susceptible to heat. Accordingly, it is desired to obtain new varieties which will have rapid growth rates, be perennial, have substantial concentrations of blooms, and which will tolerate a wide range of temperatures and growing conditions.

DESCRIPTION OF THE FIGURES

FIG. 1 shows a typical plant in hanging pot, while FIGS. 2 and 3 show respectively a cluster of flowers and a closeup of specific flowers.

BOTANICAL DESCRIPTION OF THE VARIETY

Figure 1:
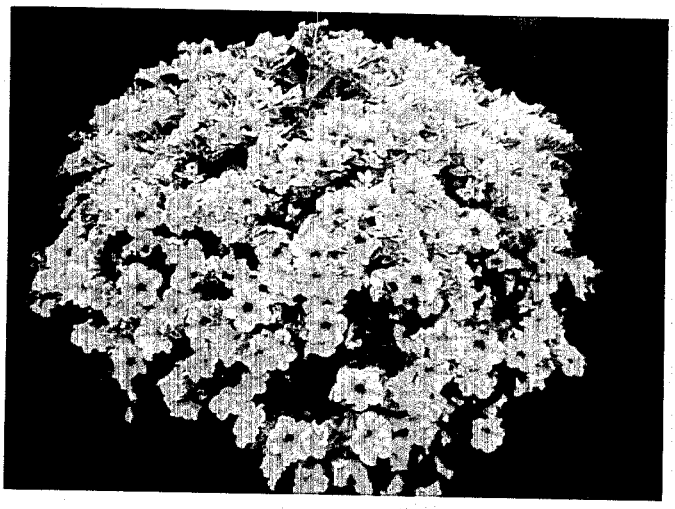
FIGS. 1, 2 and 3 are full color photographs of the new variety, taken at successively closer distances, showing the variety as grown in a nursery in Encinitas, Calif.
Figure 2:
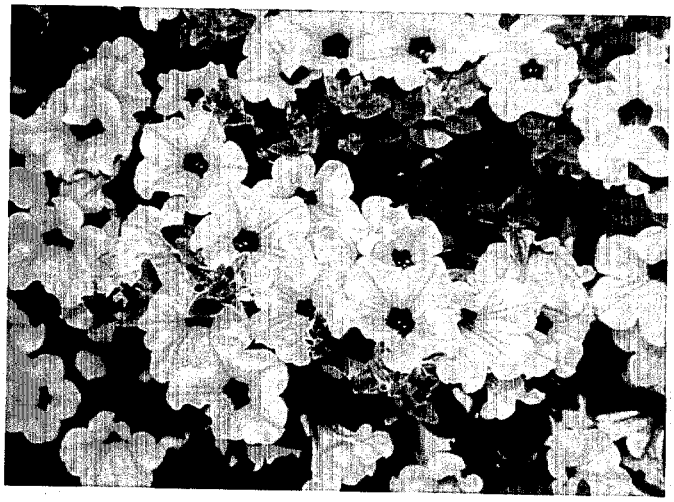
Figure 3:
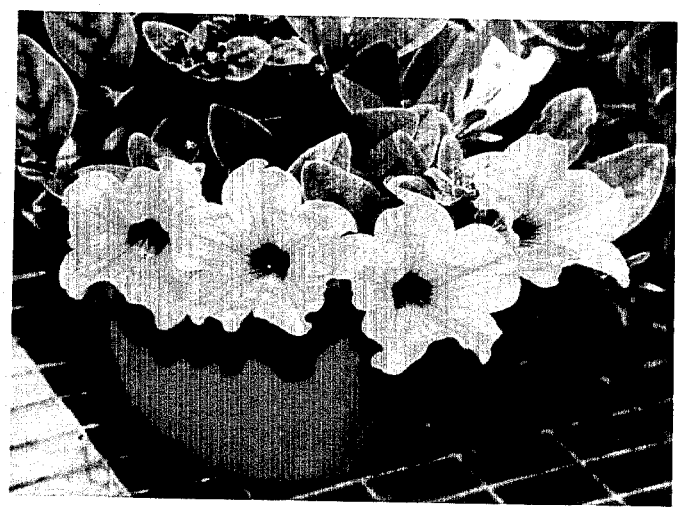

The claimed hybrid originated through open pollination of clones nos. 492X and 592Y, both respectively *Petunia axillaris* hybrids, grown in close proximity to each other at Kientzler nursery, Gensingen, Baden-Wurttemburg, Germany, and transplanted to and selected at 60 Monbulk-Emerald Road, Emerald, Victoria State, Australia. The integrity of the parent clone is preserved through asexual propagation by tip cuttings or aseptic culture. The resultant seedling progeny was grown to the flowering state and selections of clonal material were made on the basis of growth type, flower size and shape, color of foliage and flower, and spreading habit. Of the resulting plants the present "Sweet Victory" plant was selected as clearly meeting the intended goals of the propagation program.

Once the initial selections were made, another eight generations of cutting grown plants were subjected to extensive testing at the same location to insure homogeneity of the selections. Plants were tested and observed for susceptibility of fungal infestations, heat and cold endurance, performance in wet and drought conditions, flowering capability and speed of growth.

Plants vegetatively propagated and grown during the winter period in Victoria State, Australia, have proved tolerant to elevated summer ambient temperatures, up to about 113° F. (45° C.) and to chilly winter temperatures, down to slightly below 23° F. (–5° C.), for limited periods of time. The plant will not, however, survive prolonged periods of subfreezing winter temperatures or prolonged ground freezing. The optimum growing temperatures are in the range of 55°–65° F. (13°–18° C.), at which temperatures the typical growth time to mature plant is about 35 days at a daily light level in the range of 7000–9000 foot-candles (75,097 klx).

Samples of the claimed plants have also been subjected to salt spray conditions by plantings near the Pacific Ocean, in an area where extensive salt spray in the air is common. The test plants showed no visible damage over a four-month period, while plants of other genera subjected to the same conditions succumbed to the effects of the salt spray. The claimed plants may be considered to be suitable for planting in beachfront locations.

The plants are also resistant to high fertilizer concentrations which are toxic to many other types of plants. Plants will flower (in Victoria State, Australia) from early Spring through late Autumn provided that the soil pH does not exceed 6. Plants grown at Encinitas, Calif., first flower in late February to early March. At pH>6 iron deficiencies may occur which must be corrected with applications of chelated iron.

Colors described below are based on The Horticultural Colour chart of The Royal Horticultural Society, London, England.

The plants described differ in significant aspects from the most closely related plants, which are the "Pampas Fire" petunia plant selected and propogated by Applicant and the subject of a copending application for U.S. Plant Patent and the "Revolution Brilliantpink-Mini" petunia plant which is the subject of U.S. Plant Pat. No. 6,914. A comparison table identifying these differences is set out below. All measurements are mean measurements.

TABLE

| Characteristic | "Sweet Victory"[1] | "Pampas Fire" | "Revolution Brilliantpink-Mini" |
|---|---|---|---|
| Stem length, cm | 84.4 | 83.4 | 76.1 |
| Stem pubescence | much | little | medium |
| Tube width, mm[2] | 16.6 | 15.4 | 16.8 |
| Leaf length, mm[3] | 56.5 | 66.2 | 73.1 |
| Leaf shape | ovate | ovate | broad elliptic |
| Leaf color | green | green | dark green |
| Corolla diameter, mm[4] | 58.4 | 71.1 | 66.2 |
| Pedicle length, mm | 14.1 | 28.4 | 26.9 |
| Pedicle diameter, mm | 1.42 | 1.63 | 1.62 |
| Petal color outside | RHS 83D | RHS 80C | RHS 80B–82B |

[1]The claimed plant
[2]Fully opened flower, at distel end of tube
[3]Largest leaves; a few early leaves are substantially larger
[4]Fully opened flower Species: *Petunia axillaris.*

Plant:

*Type.*—Perennial, maturity being reached in four months.

*Growth habit.*—Prostrate; diffuse spreading.

*Plant height.*—15 to 20 cm.

*Spreading area of plant.*—Approximately 1 m or more.

*Blooming period.*—Early September to late May in the State of Victoria, Australia; April to September in Encinitas, Calif.

*Root system.*—Fibrous.

Stem:

*Growth habit.*—Spreading; hanging.

*Texture.*—Viscid; hirsute.

*Thickness.*—Main stem, 6 mm; lateral steam, 3 mm.

*Branching.*—Abundant; diffuse.

*Surface.*—Pubescent: glandular.

Leaf:

*Phyllotaxis.*—Long persisting.

*Arrangement.*—At first whorled, later alternate.

*Internode distance.*—5–10 mm for vegetative shoot, 20 mm for flowering shoot.

*Texture.*—Somewhat fleshy.

*Shape.*—Entire; ovate; tip of blade obtuse; base attenuate.

*Size.*—Approximately 2–6 cm long×1–2 cm wide; early leaves commonly larger than later leaves; some early leaves are exceptionally large.

*Thickness.*—0.3 to 0.5 mm.

*Color.*—Yellow green (R.H.S. 147B) above; yellow green (R.H.S. 147C) below.

Flower:

*Type.*—Axillary.

*Shape.*—Salverform; pendulous; having a hypogynous disk.

*Calyx.*—Five; parted; petals united into a tube.

*Sepal.*—Spatulate; the distal ⅓ flat, the basal ⅔ channeled; 20 mm long×8 mm wide near the rounded tip; basally adnate for 3 mm.

*Corolla.*—To 4 cm long, limb to 6 cm.

*Color.*—Red purple (R.H.S. 74A), fading to lighter red purple (R.H.S. 74C) with age; backs of petals and tube violet (R.H.S. 82D); veins of petals and tube red purple (R.H.S. 103A).

*Stamens.*—Five, four being didynamous, the fifth shortest; to 1.5 cm long; filaments pinkish yellow (R.H.S. 36D); anthers violet blue (R.H.S. 96D).

*Pedicel.*—To 3 cm long.

*Frangrance.*—Typical of *P. axillaris.*

Fruit:

*Occurrence.*—Produced rarely.

*Type.*—Capsule with two undivided valves.

Seeds:

*Occurrence.*—Produced rarely.

*Shape.*—Spherical.

*Size.*—Minute.

I claim:

1. A new and distinct variety of *Petunia axillaris* plant named "Sweet Victory" as herein illustrated and described.

* * * * *